United States Patent [19]

Payton

[11] 4,338,941

[45] Jul. 13, 1982

[54] APPARATUS FOR ARRESTING POSTERIOR NOSEBLEEDS

[76] Inventor: Hugh W. Payton, 36 S. Main St., Jeffersonville, Ohio 43404

[21] Appl. No.: 185,707

[22] Filed: Sep. 10, 1980

[51] Int. Cl.³ .............................................. A61B 17/12
[52] U.S. Cl. ................................... 128/325; 128/342; 128/344
[58] Field of Search ............... 128/342, 344, 341, 325, 128/118, 129, 296, 349 B

[56] References Cited

U.S. PATENT DOCUMENTS

| | | | |
|---|---|---|---|
| 1,051,850 | 1/1913 | Sandmark | 128/325 |
| 1,235,095 | 7/1917 | Beck | 128/325 |
| 2,265,387 | 12/1941 | McMillin | 128/342 X |
| 3,049,125 | 8/1962 | Kriwkowitsch | 128/325 |
| 3,420,237 | 1/1969 | Fortay | 128/325 |
| 3,516,407 | 6/1970 | Ruggero | 128/325 |
| 3,570,494 | 3/1971 | Gottschalk | 128/325 |
| 3,766,924 | 10/1973 | Pidgeon | 128/325 |
| 3,884,241 | 5/1975 | Walker | 128/325 |
| 4,030,504 | 6/1977 | Doyle | 128/325 |

OTHER PUBLICATIONS

Fletcher "Nasal Hemmorrhage" 106 *Medical Times*, 50–55 (1978).

*Primary Examiner*—Michael H. Thaler

*Attorney, Agent, or Firm*—Biebel, French & Nauman

[57] ABSTRACT

A posterior nasal pack has a pair of adjoining inflatable bags sharing a common wall. A U-shaped channel adapted partially to surround the posterior edge of the septum is formed by the anterior walls of the bags which walls join in a common wall at the base of the channel. The bag exterior surfaces are covered with a foamed elastomer molded to conform generally to the bony protuberances and recesses located in the posterior portion of the nasal cavity. Two flexible tubes, each attached in fluid connection with a respective bag and extending forwardly therefrom for applying a source of fluid pressure to the bags. A string attached to the posterior end of the pack aids in its removal after bleeding has been stopped.

The pack is positioned in the nasal cavity by attaching it to a pair of catheters which have been inserted into a patient's nostrils, passed through the nasopharynx, and out through the patient's mouth. As the catheters are withdrawn from the nostrils, the pack is directed into position in the nasopharynx partially surrounding the posterior edge of the septum. The attached tubes are connected to a source of fluid pressure, and the bags are inflated to expand the pack and apply hemostatic pressure to substantially all surfaces in the posterior portion of the nasal cavity.

6 Claims, 8 Drawing Figures

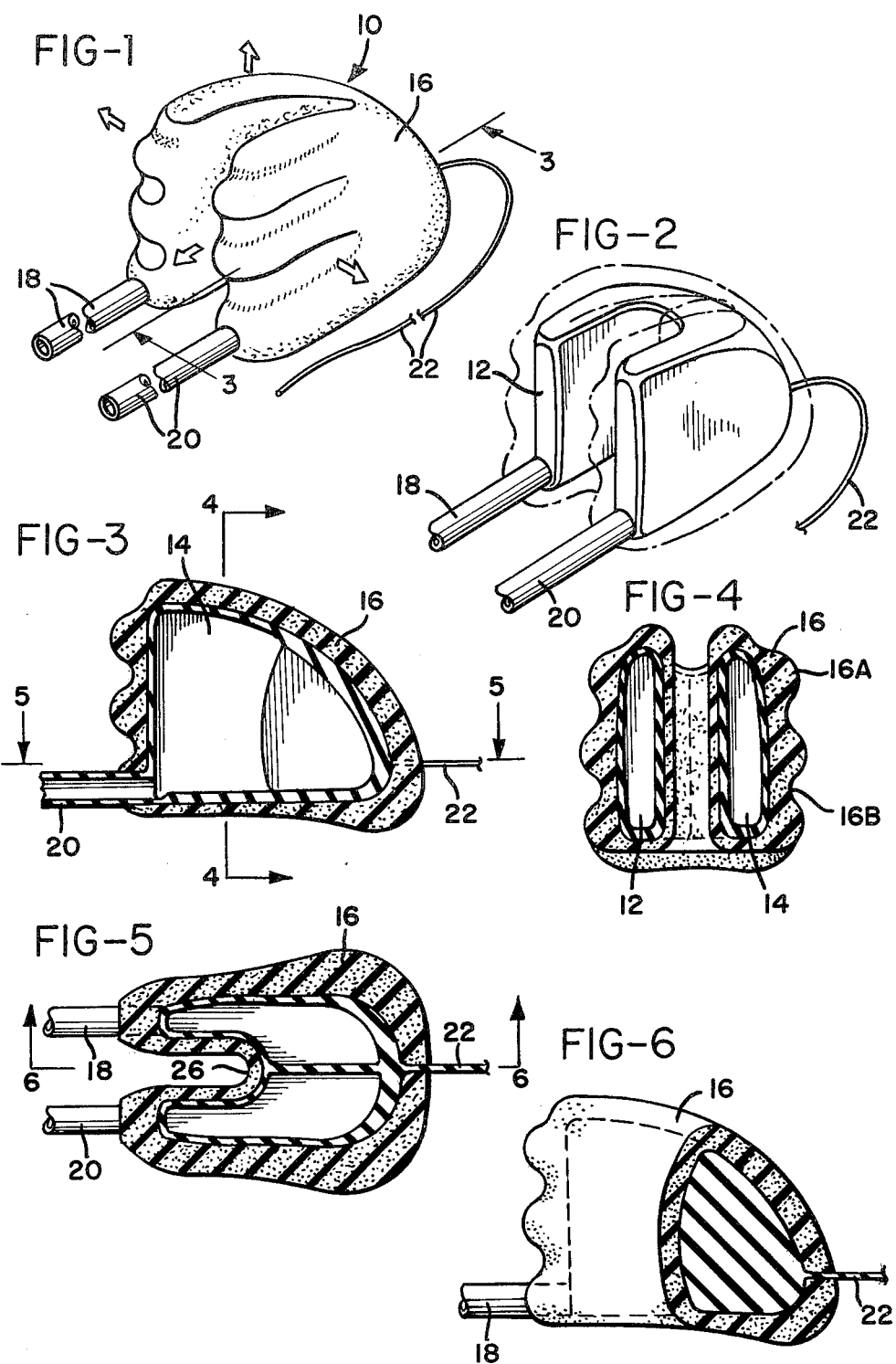

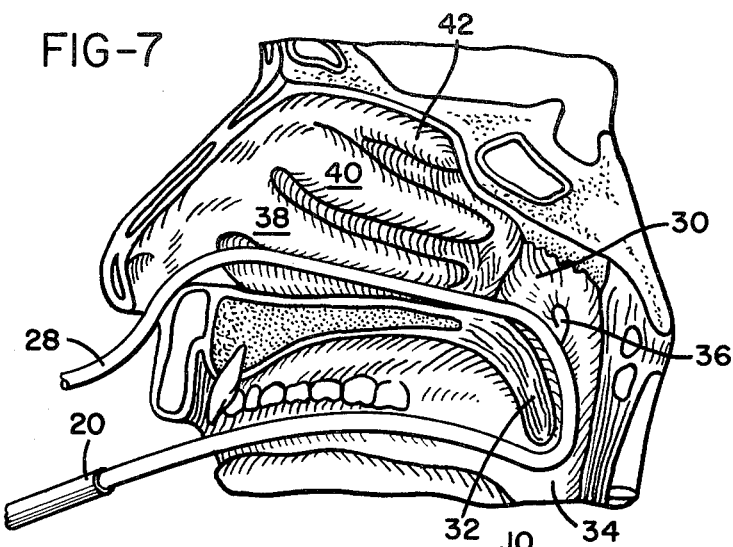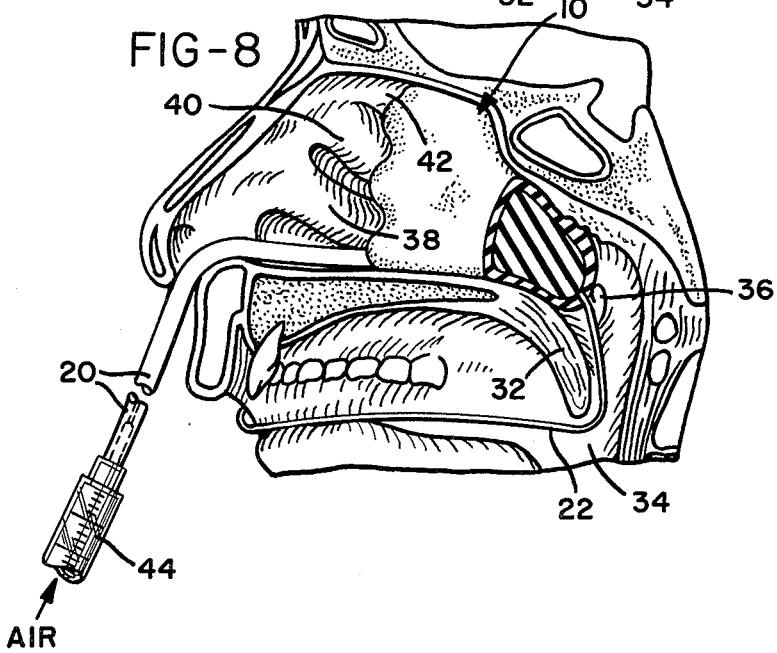

APPARATUS FOR ARRESTING POSTERIOR NOSEBLEEDS

BACKGROUND OF THE INVENTION

This invention relates generally to the treatment of nasal hemorrhages, and more particularly to an article and a method for treatment of posterior nasal hemorrhages.

Epistaxis or nasal hemorrhaging which requires packing of the nose is a common phenomenon, since branches of several major arteries are located quite close to the surfaces of the nasal cavity. Anterior hemorrhaging is relatively easy to treat by a physician because the site of the bleeding can be visually ascertained and manually treated. One of the most common methods of arresting such bleeding is chemically to cauterize the area and then insert an absorbent packing material, such as gauze or cotton, into the nasal chamber. Early workers in the art such as Sandmark, U.S. Pat. No. 1,051,850 and Beck, U.S. Pat. No. 1,235,095, utilized inflatable soft rubber balloon-like devices in place of gauze or cotton packing.

Posterior nasal hemorrhaging presents more difficult treatment problems since the source of the bleeding is both difficult to ascertain and difficult to pack properly to arrest the flow of blood. Anterior packs cannot control this type of hemorrhaging. A typical prior art procedure involves inserting flexible catheters into both nostrils of a patient through the nasopharynx and into the oropharynx. There the catheters are grasped by forceps and pulled out through the mouth. Sutures are then attached to the catheters and to a nose pack—either a piece of rolled up gauze or a tampon—and the opposite ends of the catheters are pulled slowly out of the nostrils causing the pack to move into the nasopharynx. With continued pulling of the catheters and the aid of the index finger of the physician, the pack is pulled up to a position superior to the soft palate and positioned around the posterior edge of the septum. The sutures are then tied off to hold the pack in place, and the nasal cavity is then packed by feeding gauze or other packing material into a nostril.

There have been several attempts to improve upon the basic posterior nose pack. For example, Fortay, U.S. Pat. No. 3,420,237, utilizes a thin tape of rubberized material covered by a sleeve of gauze which is positioned around the posterior end of the septum by drawing the tape through the nasal passages by use of a catheter. Walker, U.S. Pat. No. 3,884,241, provides a small, hemispherically shaped piece of foam rubber positioned posteriorly of the soft palate which acts as a stopper to prevent gauze packing in the nasal cavity from falling into the pharynx. Kriwkowitsch, U.S. Pat. No. 3,049,125, Ruggero, U.S. Pat. No. 3,516,407, Gottschalk, U.S. Pat. No. 3,570,494, and Pidgeon, U.S. Pat. No. 3,766,924, all show variations of inflatable balloon-like elements designed to be placed in a nostril and inflated to arrest nasal hemorrhaging. Doyle, U.S. Pat. No. 4,030,504, describes a porous tampon which is designed to be inserted into a nostril where it expands to assume generally the shape of the respective nasal cavity.

However, none of the above prior art devices or procedures have proved to be entirely satisfactory. Because of the nature of posterior nasal hemorrhaging, it is difficult if not impossible to pinpoint immediately the source of bleeding. Prior art devices designed to fit into a single side of a nasal cavity may or may not be effective in arresting the flow of blood depending on whether the device is inserted into the correct side of the cavity. Even if the device is inserted into the correct side of the nasal cavity, it may fail to provide proper hemostatic pressure to the ruptured blood vessels because of the numerous protruding bony areas (turbinates) in the nasal cavity underneath which blood vessels are hidden. Accordingly, the need still exists in the art for a device which will effectively arrest posterior nasal hemorrhaging by applying hemostatic pressure to all areas on both sides of the nasal cavity.

SUMMARY OF THE INVENTION

In accordance with the present invention a posterior nasal pack is provided having two separate but adjoining inflatable bags sharing a common wall and fabricated of rubber, latex, or other resilient material. The bags are covered exteriorly with a foamed elastomer, such as polyurethane foam or foam rubber or latex, and molded to conform to the posterior one-third of the nasopharynx. The pack is designed so that each inflatable bag will fit on opposite sides of the septum with the septum partially surrounded by a U-shaped channel formed by the anterior walls of the bags which join in a common wall at the base of the channel. The foamed elastomer covering the bags is molded to fit snugly around the posterior portion of the septum.

Each inflatable bag is generally rectangular in cross-section with the horizontal axis being the long axis. The posterior and lower surfaces of each bag are of thicker cross-section than the upper, lateral, and anterior wall portions, and are essentially unexpanded in use. When in position and inflated, the upper, lateral, and anterior walls of each bag expand to fill the posterior one-third of the nasopharynx and apply hemostatic pressure to the posterior portion of both sides of the nasal cavity.

All exterior surfaces of the bags are covered with a foam elastomeric material which is capable of expanding with the bags when the bags are inflated. The foam surfaces are molded to conform to the general shape of the septum, the convolutions of the turbinates, and the cribiform plate. Extending from the posterior portion of the pack and firmly attached thereto is a string or rubber band which traverses the nasopharynx, oropharynx, and the mouth and is taped to a patient's cheek externally to provide a means for easy removal of the pack. Separate flexible tubes project forward from each of the inflatable bags and have a length sufficient to project from the nostrils when the pack is in position.

The pack is placed into position, after a local anesthetic has been applied intranasally, by first inserting a flexible catheter into each nostril and through the nasopharynx region. The ends of the catheters are retrieved from the oropharynx with forceps and are attached one to each of the forwarding projecting tubes on the pack. As the catheters are withdrawn from the nostrils, the pack is directed by the physician beneath and behind the soft palate until it is firmly in place straddling the posterior portion of the septum and clear of the eustachian tube orifices. If the site of the bleeding can be located, the bag on the non-bleeding side of the nasal cavity is then moderately inflated, primarily in the anterior, lateral, and upward directions. Then the bag on the bleeding side is inflated to a point at which bleeding is arrested. Because the pack conforms to the bony structures in the nasal cavity and straddles the septum, hermorrhaging on either side will be arrested. The dual bag structure also enables more effective application of hemostatic pressure because the opposing bags provide increased lateral support to the septum. The foam rubber portion of the pack may be coated with suitable antibiotics and/or lubricants.

Accordingly, it is an object of this invention to provide an article and method for the treatment of posterior nasal hemorrhaging which will provide hemostatic pressure to all areas on both sides of the nasal cavity. This and other objects and advantages of the invention will become apparent from the following description, the accompanying drawings, and the appended claims.

BRIEF DESCRIPTION OF THE DRAWINGS

FIG. 1 is a perspective view of the posterior nasal pack;

FIG. 2 is a perspective view of the expansible bags with the foamed elastomer shown in dotted outline;

FIG. 3 is a cross-sectional, elevational view taken along line 3—3 in FIG. 1 of the nasal pack;

FIG. 4 is a cross-sectional view taken along line 4—4 in FIG. 3;

FIG. 5 is a cross-sectional, elevational view taken along line 5—5 in FIG. 3;

FIG. 6 is a cross-sectional, elevational view taken along line 6—6 in FIG. 5;

FIG. 7 is a cross-sectional, elevational view through a portion of a human head showing the insertion path of the catheters; and FIG. 8 is a cross-sectional, elevational view through a portion of a human head showing the placement of the nasal pack in operating position.

DESCRIPTION OF THE PREFERRED EMBODIMENTS

Referring now to FIGS. 1-6, a posterior nasal pack 10 made according to the invention is illustrated having a pair of inflatable, expandable bags 12 and 14, a foamed elastomer 16 covering the bags, flexible hollow tubes 18 and 20, and string 22 attached to a posterior wall of the pack. Bags 12 and 14 may be formed of any suitable flexible plastic material such as latex rubber or the like. The bags have a common interior wall 24, best shown in FIG. 5, along a portion of their long axes. The anterior portions of each bag form a U-shaped channel 26 with its base at the anterior edge of common wall 24. As best shown in FIGS. 3 and 5, the lower and posterior walls of the bags are formed with a thicker cross-section so that upon inflation these portions of the bags will expand only slightly if at all. In this manner, when the nasal pack is inflated after being positioned in the nasopharynx, it will principally expand in the upward, forward, and outward directions indicated by the arrows in FIG. 1.

Covering all of the surfaces of bags 12 and 14 and adhered thereto is a foamed elastomeric material 16. This material may be any conventional flexible foamed material such as foam rubber, polyurethane, or the like. Foamed elastomer 16 is molded with ridges 16A and identations 16B so that it generally conforms to the projecting bony regions called turbinates located in the nasopharynx. In this manner, expansion of bags 12 and 14 causes a similar expansion of foamed elastomer 16 around the superior, middle, and inferior turbinates and into the meatus regions in the nasopharynx enabling the nasal pack to exert an even hemostatic pressure on all surfaces, even to those areas normally hidden in cavities between the bony regions.

Alternatively, the bags 12 and 14 and foamed elastomer 16 may be formed in a single operation by molding a closed-cell foam in the shape of nasal pack 10. In place of bags 12 and 14 would be fluid-impervious inner walls.

Flexible, hollow tubes 18 and 20 are attached to the anterior walls of bags 12 and 14, respectively, and are in fluid connection with the interior of each respective bag. These tubes are of sufficient length to extend forwardly of the nasal pack through the nasal cavity and out the nostrils of a patient. There they can be attached to a source of fluid pressure such as air or water which serves to inflate bags 12 and 14.

A string 22, which can be made of rubber or any conventional suture material, is attached to the posterior portion of the nasal pack 10. Alternatively, string 22 may be integrally formed with bags 12 and 14. String 22 preferably has a length sufficient to traverse the nasopharynx, oropharynx, and mouth of a patient so that may be taped to the exterior of a patient's cheek. This string greatly aids in the removal of the nasal pack once it has served its purpose. In removing the pack, tubes 18 and 20 are detached from any source of fluid pressure, the pack deflated, and the string 22 gently pulled by the physician to displace the pack from the nasopharynx region and remove it through the patient's mouth.

To improve the performance of the pack it may be coated or impregnated with anti-stick coatings, lubricants, antibiotics, or the like. Anti-stick polymeric coatings or lubricants such as petrolatum prevent the pack from sticking to clotted blood or the scab which forms over the hemorrhaged area and renders removal of the pack much easier and lessens the danger of causing hemorrhaging to start again. Coating or impregnating the pack with an antibiotic preparation such as penicillin, streptomycin, or terramycin prevents or reduces the occurrence of local infections and prevents odor.

Referring now to FIGS. 7 and 8, the posterior nasal pack of the present invention is positioned in the following manner. Initially, the nasal mucosa of the patient is anesthetized by the topical application of a local anesthetic such as a 10 percent cocaine solution on a cotton applicator. Cocaine is also a vasoconstrictor and aids in decreasing the bleeding. A pair of flexible catheters 28 (only one illustrated), one in each nostril, are then inserted into and through the left and right sides of the nasal cavity, through the nasopharynx 30 over the soft palate 32 and down into the oropharynx 34. The catheters 28 are then retrieved using forceps, pulled through the patient's mouth.

The nasal pack is then attached to the catheters 28 at tubes 18 and 20. Tubes 18 and 20 may be sized such that they may frictionally fit over catheters 28. Alternatively, sutures may be used to tie the tubes to the catheters. Care must be taken to attach correctly the nasal pack to the catheters in an inverted position so that it will be in its correct upright position in the nasopharynx.

The physician then pulls catheters 28 from the nostrils while guiding the nasal pack with an index finger under the soft palate and into position in the nasopharynx. Care must be taken when positioning the nasal pack that the eustachian tube orifices 36 on either side of nasopharynx are not blocked by the pack. This could lead to an ear infection or other problems. The U-shaped channel 26 is designed to straddle and partially surround the posterior portion of the septum when the pack is properly positioned. The ridges and indentations on the foamed elastomer will conform generally to the inferior, middle, and superior turbinates of the lateral wall 38, 40, 42 and the meatus areas therebetween.

Once positioned, a source of a fluid 44, such as air, under pressure is attached to tubes 18 and 20 to inflate bags 12 and 14. As shown in FIG. 8, the pack will expand forwardly, upwardly, and outwardly to apply hemostatic pressure to the walls of the nasopharynx. Many posterior nasal hemorrhages occur along branches of the sphenophalatine artery in the inferior meatus under the inferior turbinate. Because of the molded shape of the foamed elastomer on the nasal pack, application of hemostatic pressure is greatly simplified. Additionally, in a preferred method of arresting a nasal hemorrhage, the inflatable bag on the side opposite the bleeding is initially moderately inflated to provide lateral pressure on the septum. Then the second bag is inflated to the degree necessary to stop the bleeding with the opposite bag providing lateral support, thereby offering increased hemostatic pressure to bleeding sites. Additionally, with independently controlled inflatable bags, the physician can deflate the bag on the non-bleeding side of the nasal cavity after a period of time to determine whether bleeding has been completely arrested. The unique dual-bag structure of the posterior nasal pack of this invention in combination with the molded foamed elastomer results in increased stability of the pack when positioned, as well as the ability to apply hemostatic pressure to substantially all potential bleeding sites in the posterior one-third of the nasopharynx.

It is within the scope of this invention to eliminate common wall 24 to provide a single fluid inflatable chamber in nasal pack 10. In this embodiment, bags 12 and 14 are in fluid communication with each other, and only a single hollow tube 18 is required to inflate the pack. To aid in the positioning of the pack, however, tube 20 may be replaced by a string or rubber band such that it will project from a patient's nostril and can be manipulated by the physician.

While the apparatus and methods herein described constitute preferred embodiments of the invention, it is to be understood that the invention is not limited to these precise apparatus and methods, and that changes may be made in either without departing from the scope of the invention, which is defined in the appended claims.

What is claimed is:

1. A posterior nasal pack device adapted to be inserted through the mouth and oropharynx of a patient into the nasopharynx partially surrounding the posterior portion of the septum and thereafter expanded to apply hemostatic pressure to arrest posterior nasal hemorrhaging comprising;

an expandable, foamed elastomer pack molded to conform generally to the surfaces of the walls of both sides of the posterior portion of the nasal cavity, the anterior wall of said pack having a U-shaped channel adapted to partially surround the posterior end of the septum with the respective ends of said U-shaped channel extending into opposite sides of the nasal cavity prior to expansion, the interior of said elastomer pack containing two adjoining hollow, fluid impermeable chambers sharing a common wall, tube means attached to the anterior wall of said elastomer pack said tube means comprising a first and second hollow, flexible tube, each of said first and second tubes in fluid communication with a respective hollow chamber, and string means attached to said elastomer pack of sufficient length to traverse the distance between the nasopharynx and the mouth to aid in removal of the nasal pack.

2. A posterior nasal pack device adapted to be inserted into the nasopharynx partially surrounding the posterior portion of the septum and thereafter expanded to apply hemostatic pressure to arrest posterior nasal hermorrhaging comprising, a first and second hollow expandable bag, each having a generally rectangular cross-section along a vertical section, said first bag having a common wall with said second bag along at least a portion of their interior side walls, the remaining portion of the respective interior side walls forming a U-shaped channel adapted to partially surround the posterior end of the septum, an expandable foamed elastomeric material adhered to all exterior surfaces of said bags and molded to conform generally to the surfaces of the walls of the nasal cavity, a first and second hollow, flexible tube, said first and second tubes attached to a respective anterior wall of said first and second expansible bags and in fluid communication with the interior of each of the respective bags, and a string attached to one of said expansible bags of sufficient length to traverse the distance between the nasopharynx and the mouth to aid in removal of said nasal pack.

3. The nasal pack of claim 2 in which the bottom and posterior walls of said first and second bags have a thicker cross-section than the upper and anterior walls.

4. The nasal pack of claim 3 in which said first and second bags are expansible upwardly, forwardly, and outwardly upon the internal application of pressurized fluid.

5. The nasal pack of claim 2 in which said foamed elastomeric material is coated with a lubricant.

6. The nasal pack of claim 2 in which said foamed elastomeric material is coated with an antibiotic.

* * * * *